United States Patent
Yoshida et al.

(10) Patent No.: US 10,993,966 B2
(45) Date of Patent: May 4, 2021

(54) PLURIPOTENT STEM CELL FOR TREATMENT OF CEREBRAL INFARCTION

(71) Applicants: LIFE SCIENCE INSTITUTE, INC., Tokyo (JP); TOHOKU UNIVERSITY, Sendai (JP)

(72) Inventors: Masanori Yoshida, Akita (JP); Mari Dezawa, Sendai (JP); Teiji Tominaga, Sendai (JP)

(73) Assignees: LIFE SCIENCE INSTITUTE, INC., Tokyo (JP); TOHOKU UNIVERSITY, Sendai (JP)

( * ) Notice: Subject to any disclaimer, the term of this patent is extended or adjusted under 35 U.S.C. 154(b) by 0 days.

(21) Appl. No.: 15/413,086

(22) Filed: Jan. 23, 2017

(65) Prior Publication Data

US 2017/0128494 A1 May 11, 2017

Related U.S. Application Data

(63) Continuation of application No. 14/695,843, filed on Apr. 24, 2015.

(30) Foreign Application Priority Data

Feb. 26, 2014 (JP) .............................. JP2014-035725

(51) Int. Cl.
*A61K 35/28* (2015.01)
*A61K 35/545* (2015.01)

(52) U.S. Cl.
CPC ............ *A61K 35/28* (2013.01); *A61K 35/545* (2013.01)

(58) Field of Classification Search
CPC ......... A61K 35/28; A61K 35/545; A61P 9/10; A61P 9/00; A61P 43/00; A61P 25/28; A61P 25/00
See application file for complete search history.

(56) References Cited

U.S. PATENT DOCUMENTS

2006/0210544 A1* 9/2006 Honmou ................ A61K 35/28
424/93.21
2011/0070647 A1* 3/2011 Dezawa ............... C12N 5/0607
435/378

FOREIGN PATENT DOCUMENTS

WO    2011/007900 A1    1/2011

OTHER PUBLICATIONS

Yamauchi et al. "Therapeutic effects of human multilineage-differentiating stress enduring (MUSE) cell transplantation into infarct brain of mice." PLoS One. Mar. 6, 2015;10(3):e0116009.*
Kawabori et al. "Intracerebral, but not intravenous, transplantation of bone marrow stromal cells enhances functional recovery in rat cerebral infarct: an optical imaging study." Neuropathology. Jun. 2012;32(3):217-26. (Year: 2012).*
Thomson et al. "Embryonic stem cell lines derived from human blastocysts."Science. Nov. 6, 1998;282(5391):1145-7. (Year: 1998).*
Kuroda et al. "Unique nnultipotent cells in adult human mesenchymal cell populations."Proc Natl Acad. Sci U S A. May 11, 2010;107(19):8639-43 (Year: 2010).*
Dezawa M. "Muse Cells Provide the Pluripotency of Mesenchymal Stem Cells: Direct Contribution of Muse Cells to Tissue Regeneration . . . " Cell Transplant. 2016;25(5):849-61. (Year: 2012).*
Kuroda et al. "Unique nnultipotent cells in adult human mesenchymal cell populations."PNAS May 11, 2010. 107 (19) 8639-8643 (Year: 2010).*
Fisch et al. "Pluripotent nontumorigenic multilineage differentiating stress enduring cells (Muse cells): a seven-year retrospective." Stem Cell Res Ther. Oct. 18, 2017;8(1):227 (Year: 2017).*
Kes et al. "Etiology and diagnostic work-up in young stroke patients." Periodicum Biologorum (2012) 57:61 vol. 114, No. 3, 355-359, (Year: 2012).*
Special Report From the National Institute of Neurological Disorders and Stroke, "Classification of Cerebrovascular Diseases III," *Stroke* (Apr. 1990), 21(4):637-676.
The National Institute of Neurological Disorders and Stroke rt-Pa Stroke Study Group, "Tissue Plasminogen Activator for Acute Ischemic Stroke," *The New England Journal of Medicine* (Dec. 14, 1995), 333(24):1581-1587.
Kuroda, Yasumasa et al., "Unique multipotent cells in adult human mesenchymal cell populations," *PNAS* (May 11, 2010), 107(19):8639-8643.
Kuroda, Yasumasa et al., "Isolation, culture and evaluation of multilineage-differentiating stress-enduring (Muse) cells," *Nature Protocols* (published online Jun. 20, 2013); 8(7):1391-1415.
Sinden, John D. et al. "Stem cells in stroke treatment: the promise and the challenges," *International Journal of Stroke* (Jul. 2012), 7:426-434.
Wakao, Shohei et al., "Multilineage-differentiating stress-enduring (Muse) cells are a primary source of induced pluripotent stem cells in human fibroblasts," *PNAS* (Jun. 14, 2011), 108(24):9875-9880.
Honma et al., "Intravenous administration of human mesenchymal stem cells.", Neuroscience, Nov. 12, 2003, Presentation No. 788.11, Transplantation & Disease, Abstract, 2 pages.
Wei et al., "Transplantation of Hypoxia Preconditioned Bone Marrow Mesenchymal Stem Cells Enhances Angiogenesis and Neurogenesis after Cerebral Ischemia in Rats," Neurobiol. Dis., Jun. 2012, 46(3), pp. 635-645.

* cited by examiner

*Primary Examiner* — Titilayo Moloye
(74) *Attorney, Agent, or Firm* — Kilpatrick Townsend & Stockton, Inc.

(57) ABSTRACT

An object of the present invention is to provide a novel medical application to regenerative medicine that uses pluripotent stem cells (Muse cells). The present invention provides a cell preparation for treating cerebral infarction and sequelae associated therewith that contains SSEA-3-positive pluripotent stem cells isolated from mesenchymal tissue in the body or cultured mesenchymal cells. The cell preparation of the present invention is based on a brain tissue regeneration mechanism by which Muse cells differentiate into nerve cells and the like in damaged brain tissue by administering Muse cells into cerebral parenchyma.

24 Claims, 4 Drawing Sheets

PLURIPOTENT STEM CELL FOR TREATMENT OF CEREBRAL INFARCTION

CROSS-REFERENCE TO RELATED APPLICATIONS

The current application is a continuation of U.S. patent application Ser. No. 14/695,843, filed Apr. 24, 2015, pending, which application claims priority to JP 2014-035725, filed Feb. 26, 2014, the disclosures of which are hereby incorporated by reference in their entireties for all purposes.

FIELD OF INVENTION

The present invention relates to a cell preparation used in regenerative medicine. More specifically, the present invention relates to a cell preparation containing pluripotent stem cells that are effective for repairing and regenerating brain tissue that has been damaged by cerebral infarction.

BACKGROUND OF THE INVENTION

Cerebral infarction refers to a brain dysfunction that occurs due to ischemic necrosis localized in the brain, requires emergency treatment, and is one of the three leading causes of death after cancer and heart disease. In terms of its mechanism of action, cerebral infarction is categorized as thrombotic, embolic or hemodynamic cerebral infarction, or is classified into categories such as atherothrombotic cerebral infarction, cardiogenic embolism or lacunar infarction from the perspective of clinical findings.

Ischemia occurs due to a local interruption of cerebral blood flow caused by a cerebrovascular lesion such as arteriosclerosis or cardiogenic thromboembolism, and nerve cell death is induced at the ischemic core due to energy depletion. In the area around the ischemic core, blood flow remains by means of collateral circulation, and although nerve cells are not functioning in terms of electrophysiology, they remain in a viable state. Nerve cells in this area eventually end up undergoing necrosis unless treatment is performed, and in pathological terms, the infracted area progresses and clinically results in the disorder of cerebral dysfunction. Accordingly, cerebral dysfunction can be treated provided the function of nerve cells in the affected area can be restored as quickly as possible. This reversible region of incomplete ischemia is referred to as the penumbra. The purpose of treating the acute stage of cerebral infarction is to restore the function of nerve cells in this penumbra region, and the outcome thereof is dependent upon the degree of ischemia and its duration. Namely, outcome is determined by how quickly blood flow can be resumed to the penumbra region. Nerve cells in this penumbra region are believed to be able to survive for 3 to 6 hours following an attack. In addition, the allowed amount of time during which the function of nerve cells in a penumbra region can be restored by treatment is referred to as treatment time (Stroke, Vol. 21, p. 637-676 (1990)).

At present, thrombolytic therapy using recombinant human plasminogen activator (rt-PA), which has been approved in the U.S. for use in the treatment of acute stage cerebral infarction, was developed for the purpose of restoring blood flow to a penumbra region by lysing thrombi causing ischemia. In studies on rt-PA therapy by intravenous injection targeted at cerebral infarction patients within 3 hours after an attack, outcomes were significantly more favorable after 3 months in an rt-PA dose group in a double-blind placebo-controlled clinical trial conducted in the U.S. rt-PA is thought to improve dysfunction caused by cerebral infarction by enabling resumption of the supply of blood to an ischemic region and inhibiting the progression of cerebral infarction by lysing thrombi. This result indicated that early resumption of cerebral blood flow by thrombolytic action improves long-term prognosis (N. Eng. J. Med., Vol. 333, p. 1581-1587 (1995)). In addition, although stem cell therapy is expected to be a new treatment method used in the treatment of cerebral infarction in addition to using thrombolytic therapy as described above, it has yet to demonstrate adequate therapeutic effects and is currently not established as a treatment method (Sinden, J. D. & Muir, K. W., Vol. 7, p. 426-434 (2012)).

It has been determined from research by M. Dezawa, one of the inventors of the present invention, that multilineage-differentiating stress enduring cells (Muse cells) expressing surface antigen in the form of stage-specific embryonic antigen-3 (SSEA-3), which are present in mesenchymal cell fractions and can be obtained without going through an induction procedure, are responsible for the pluripotency possessed by mesenchymal cell fractions, and that they have the potential for application to disease treatment aimed at tissue regeneration. In addition, Muse cells were also determined to be able to be concentrated by stimulating mesenchymal cell fractions with various types of stress (WO2011/007900; Kuroda, Y., et al., Proc. Natl. Acad. Sci. USA, Vol. 107, p. 8639-8643 (2010); Wakao, S., et al., Proc. Natl. Acad. Sci. USA, Vol. 108, p. 9875-9880 (2011); Kuroda, Y., et al., Nat. Protoco., Vol. 8, p. 1391-1415 (2013)). However, there have yet to be any examples of the use of Muse cells for the treatment of cerebral infarction, and the obtaining of anticipated therapeutic effects has yet to be clearly determined.

SUMMARY

An object of the present invention is to provide a novel medical application to regenerative medicine that uses pluripotent stem cells (Muse cells). More specifically, an object of the present invention is to provide a cell preparation for prevention and/or treatment of cerebral infarction and sequelae occurring in association therewith (including movement impairment, sensory impairment and speech impairment) that contains Muse cells.

Means for Solving the Problems

The inventors of the present invention found that, by injecting Muse cells into the cerebral parenchyma of a rat cerebral infarction model induced by ischemia-reperfusion by inserting an embolus into a cerebral blood vessel, the Muse cells survive over the course of several months after taking to damaged brain tissue and bring about a reduction in infarct size along with improvement or restoration of brain function as a result of spontaneously differentiating into brain cells, thereby leading to completion of the present invention.

Namely, the present invention is as described below.

[1] A cell preparation for treating cerebral infarction, containing pluripotent stem cells positive for SSEA-3 isolated from biological mesenchymal tissue or cultured mesenchymal cells.

[2] The cell preparation according to [1] and [2] above, for preventing and/or treating sequelae from cerebral infarction.

[3] The cell preparation according to [1] above, wherein the pluripotent stem cells positive for SSEA-3 contain a concentrated cell fraction as a result of stimulation by external stress.

[4] The cell preparation according to [1] to [3] above, wherein the pluripotent stem cells are CD105-positive.

[5] The cell preparation according to [1] to [4] above, wherein the pluripotent stem cells are CD117-negative and CD146-negative.

[6] The cell preparation according to [1] to [5] above, wherein the pluripotent stem cells are CD117-negative, CD146-negative, NG2-negative, CD34-negative, vWF-negative and CD271-negative.

[7] The cell preparation according to [1] to [6] above, wherein the pluripotent stem cells are CD34-negative, CD117-negative, CD146-negative, CD271-negative, NG2-negative, vWF-negative, Sox10-negative, Snail-negative, Slug-negative, Tyrp1-negative and Dct-negative.

[8] The cell preparation according to [1] to [7] above, wherein the pluripotent stem cells are pluripotent stem cells having all of the properties indicated below:
(i) low or absent telomerase activity;
(ii) ability to differentiate into any of the three germ layers;
(iii) absence of demonstration of neoplastic proliferation; and,
(iv) self-renewal ability.

[9] The cell preparation described in [1] to [8] above, wherein the pluripotent stem cells have the ability to differentiate into one or more cells selected from the group consisting of nerve cells, glial cells, vascular endothelial cells, and/or microglial cells.

The present invention is able to dramatically reduce infarct size by a mechanism involving regeneration of brain tissue in which Muse cells differentiate cells that compose brain tissue in damaged brain tissue by being administered to the cerebral parenchyma of a subject suffering from cerebral infarction.

BRIEF DESCRIPTION OF THE DRAWINGS

FIG. 3 indicates the results of measuring somatosensory evoked potential (SEP) in a rat cerebral infarction model 85 days after injecting Muse cells and the like.

DETAILED DESCRIPTION

Figure 1:
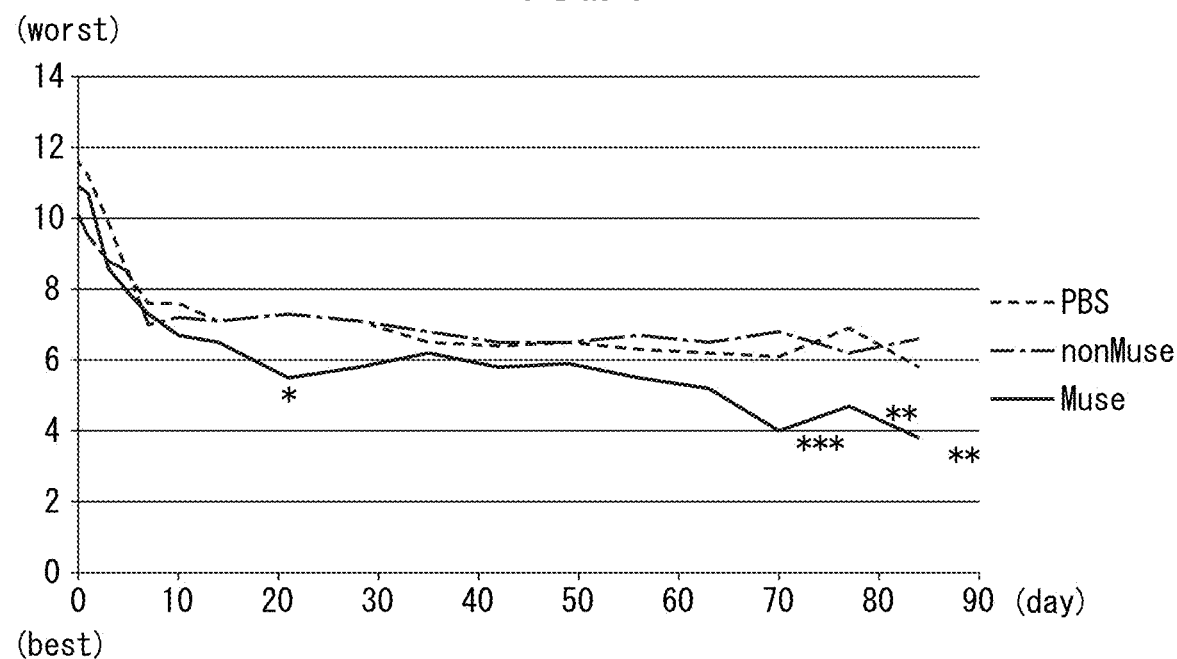
FIG. 1 indicates the results of evaluating neurological severity score (NSS) over the course of three months following injection of Muse cells derived from human skin fibroblasts, human skin fibroblasts from which Muse cells had been removed (namely, non-Muse cells) or phosphate-buffered saline (PBS) into the cerebral parenchyma of a rat cerebral infarction model. A decrease in score value on the vertical axis corresponds to recovery of brain function.

The present invention relates to a cell preparation for treating cerebral infarction that contains SSEA-3-positive pluripotent stem cells (Muse cells). The following provides a detailed explanation of the present invention.

1. Applicable Diseases

The present invention aims to treat cerebral infarction using a cell preparation containing SSEA-3-positive pluripotent stem cells (Muse cells). Here, "cerebral infarction" is a state that ischemic area is locally generated in brain by obstruction or perfusion pressure decrease of cerebral blood vessel whereby an irreversible necrosis of neurons occurs. It is preferably an acute brain infarction phase within 48 hours of the infarction onset, more preferably within 24 hours, still more preferably within 6 hours and, most preferably, cerebral infraction within 3 hours of the infraction onset. Here, the term "onset" is defined as the time that which the patient was last seen in a normal state, or bedtime for unwitnessed cerebral infraction occurring during the night. Due to the cause of thrombus, cerebral infarction is classified into cerebral thrombus and cerebral embolism and the present invention is useful for the therapy of cerebral thrombus and cerebral embolism. The term "therapy of cerebral infraction" means an effect of preventing the progress of infarct foci in an acute phase of cerebral infraction, an effect of improving the dysfunction or the subjective symptom accompanied by cerebral infarction and/or an effect of preventing the occurrence of psychiatric symptom and convulsion onset during a chronic phase. It further includes prevention of recurrence of the onset of cerebral infraction. In addition, according to the observation by CT prior to the administration, degree of cerebral infarction may be classified depending upon infarct size, extent of infarct foci (penetrating branch and cortical branch), side of infarct (left, right or both), region of infarct (anterior cerebral artery region, middle cerebral artery region, posterior cerebral artery region, watershed region, brain stem, cerebellum and others) and degree of edema. The term "suppression of the progress of cerebral infraction" means an effect that expansion of infarct nidus with a lapse of time after the onset of ischemic event is suppressed as compared with the untreated case. The term "reducing effect of cerebral infarction" means that the volume of infract foci generated by cerebral infarction, which was measured prior to administration of the cell preparation according to the present invention, is reduced at an evaluation point after a certain period of time following the administration of the cell preparation. Further, the cell preparation according to the present invention can be used in prevention and/or treatment of sequelae from cerebral infarction. Here, "sequelae" includes speech and language disorder, disturbance of perception such as numbness, disorder of movement in a limb, headache, vomiting, visual loss, deglutition disorder, articulation disorder, dementia and the like.

2. Cell Preparation
(1) Pluripotent Stem Cells (Muse Cells)

The existence of the pluripotent stem cells used in the cell preparation of the present invention in the body was discovered by M. Dezawa, one of the applicants of the present invention, and the cells were named "multilineage-differentiating stress enduring (Muse) cells". Muse cells can be obtained from bone marrow, adipose tissue (Ogura, F., et al., Stem Cells Dev., Nov. 20, 2013 (Epub) (published on Jan. 17, 2014), or skin tissue such as dermal connective tissue, and are sporadically present in the connective tissue of various organs. In addition, these cells have both the properties of pluripotent stem cells and mesenchymal stem cells, and are identified as being double-positive for each of the cell surface markers of pluripotent stem cells, "stage-specific embryonic antigen-3 (SSEA-3)" and of mesenchymal stem cells such as "CD105". Thus, Muse cells or cell populations containing Muse cells can be isolated from body tissue, for example, by using these antigen markers as indicators. Details regarding methods used to isolate and identify Muse cells as well as their characteristics are disclosed in International Publication No. WO2011/007900. In addition, as has been reported by Wakao, et al. (2011, previously cited), in the case of using a cell culture obtained by culturing mesenchymal cells present in bone marrow, skin and the like as the parent population of Muse cells, all cells positive for SSEA-3 are known to be positive for CD105. Thus, in the cell preparation of the present invention, in the case of isolating Muse cells from biological mesenchymal tissue or cultured mesenchymal cells, Muse cells can be purified and used simply by using SSEA-3 as an antigen marker. Furthermore, in the present description, pluripotent stem cells (Muse cells) able to be used in a cell preparation for treating cerebral infarction (including sequelae) that have been isolated from biological mesenchymal tissue or cultured mesenchymal cells by using SSEA-3 as an antigen marker, or a cell population containing Muse cells, may simply be described as "SSEA-3-positive cells". In addition, In the present specification, "non-Muse cells" means cells included in biological mesenchymal tissue or cultured mesenchymal cells, which are not "SSEA-3-positive cells."

Simply speaking, Muse cells or cell populations containing Muse cells can be isolated from biological tissue (such as mesenchymal tissue) using antibody to the cell surface marker SSEA-3 alone or using antibody to SSEA-3 and CD105, respectively. Here, "biological tissue" refers to the biological tissue of a mammal. In the present invention, although an embryo in a development stage prior to a fertilized egg or blastula stage is not included in biological tissue, an embryo in a development stage in or after the fetus or blastula stage, including the blastula, is included. Examples of mammals include, but are not limited to, primates such as humans or monkeys, rodents such as mice, rats, rabbits or guinea pigs as well as cats, dogs, sheep, pigs, cows, horses, donkeys, goats and ferrets. The Muse cells used in the cell preparation of the present invention are clearly distinguished from embryonic stem (ES) cells and embryonic germ (EG) cells in that they are directly collectable from biological tissue and are non-tumorigenic. In addition, "mesenchymal tissue" refers to tissue such as bone, synovial membrane, fat, blood, bone marrow, skeletal muscle, dermis, ligaments, tendons, tooth pulp, umbilical cord, umbilical cord blood, as well as tissues present in various organs. For example, Muse cells can be obtained from bone marrow, skin or fat tissue. For example, Muse cells are preferably used that have been isolated from mesenchymal tissue collected from the living body. In addition, Muse cells may also be isolated from cultured mesenchymal cells such as fibroblasts or bone mallow mesenchymal cells using the aforementioned isolation means. Furthermore, Muse cells used in the cell preparation of the present invention may be autologous or allogenic relative to the recipient who receives the cell transplant.

As has been described above, although Muse cells or cell populations containing Muse cells can be isolated from biological tissue by using their property of being SSEA-3-positive and CD105-positive, human adult skin is known to contain various types of stem cells and precursor cells. However, Muse cells are not the same as these cells. Examples of such stem cells and precursor cells include skin-derived precursor (SKP) cells, neural crest stem cells (NCSC), melanoblasts (MB), perivascular cells (PC), endothelial precursor (EP) cells and adipose-derived stem cells (ADSC). Muse cells can be isolated from these cells by using "non-expression" of a unique marker as an indicator of these cells. More specifically, Muse cells can be isolated by using non-expression of at least one of 11 markers, such as 1, 2, 3, 4, 5, 6, 7, 8, 9, 10 or 11 markers, selected from the group consisting of CD34 (marker for EP and ADSC), CD117 (c-kit) (MB marker), CD146 (PC and ADSC marker), CD271 (NGFR) (NCSC marker), NG2 (PC marker), vWF factor (von Willebrand factor) (EP marker), Sox10 (NCSC marker), Snail (SKP marker), Slug (SKP marker), Tyrpl (MB marker) and Dct (MB marker). For example, although not limited thereto, Muse cells can be isolated by using non-expression of CD117 and CD146 as an indicator, can be isolated using non-expression of CD117, CD146, NG2, CD34, vWF and CD271 as an indicator, and can be isolated by using non-expression of the aforementioned 11 markers as an indicator.

In addition, Muse cells having the aforementioned characteristics used in the cell preparation of the present invention may have at least one property selected from the group consisting of:

(i) low or absent telomerase activity;

(ii) ability to differentiate into any of the three germ layers;

(iii) absence of demonstration of neoplastic proliferation; and, (iv) self-renewal ability.

In one aspect of the present invention, the Muse cells used in the cell preparation of the present invention have all of the aforementioned properties. Here, with respect to the aforementioned (i), "low or absent telomerase activity" refers to telomerase activity being low or being unable to be detected in the case of having detected telomerase activity using, for example, the Trapeze XL Telomerase Detection Kit (Millipore Corp.). "Low" telomerase activity refers to having telomerase activity roughly equal to that of human fibroblasts, for example, or having telomerase activity that is ⅕ or less and preferably ⅒ or less in comparison with Hela cells. With respect to the aforementioned (ii), Muse cells have the ability to differentiate into the three germ layers (endoderm, mesoderm and ectoderm) in vitro and in vivo, and by inducing to differentiate by culturing in vitro, for example, can differentiate into skin, liver, nerve, muscle, bone or fat and the like. In addition, Muse cells may also demonstrate the ability to differentiate into the three germ layers in the case of transplanting in vivo into testes, for example. Moreover, Muse cells also have the ability to migrate, graft and differentiate into a damaged organ (such as the heart, skin, spinal cord, liver or muscle) by being transplanted into the body by intravenous injection. With respect to the aforementioned (iii), although Muse cells proliferate in a suspension culture, they have the property of discontinuing proliferation for about 10~14 days. In adherent culture, their doubling time is approximately 1.3 days/cell division which is similar to human fibroblasts, and keep proliferating until cell reach nearly to Heyflick limit. Thus, in the case of having been transplanted into testes, have the property of not becoming malignant for at least six months. In addition, with respect to the aforementioned (iv), Muse cells have self-renewal (self-replication) ability. Here, "self-renewal" refers to culturing cells contained in an embryoid body-like cell mass obtained by suspension culturing single Muse cell and allowing them to reform an embryoid body-like cell mass from a single cell again as well as to demonstrate spontaneous differentiation of embryoid body-like cell mass into triploblastic cell lineages on gelatin coated culture. Self-renewal may be carried out for one cycle or repeated for a plurality of cycles.

(2) Preparation and Use of Cell Preparation

The cell preparation of the present invention, although not limited thereto, is obtained by suspending Muse cells or a cell population containing Muse cells obtained in the aforementioned (1) in physiological saline or a suitable buffer (such as phosphate-buffered physiological saline). In this case, in the case the number of Muse cells isolated from autologous or allogenic tissue is low, cells may be cultured prior to cell transplant and allowed them to proliferate until a prescribed cell concentration is obtained. Furthermore, as has been previously reported (International Publication No. WO 2011/007900), since Muse cells do not undergo neoplastic transformation, there is little likelihood of the cells becoming malignant even if cells recovered from biological tissue are contained that have still not differentiated, thereby making them safe. In addition, although there are no particular limitations thereon, culturing of recovered Muse cells can be carried out in an ordinary growth medium (such as minimum essential medium-α (α-MEM) containing 10% bovine calf serum). More specifically, a solution containing a prescribed concentration of Muse cells can be prepared by selecting media, additives (such as antibiotics and serum) and the like suitable for the culturing and proliferation of Muse cells with reference to the aforementioned International Publication No. WO2011/007900. In the case of administering the cell preparation of the present invention to a human, roughly several milliliters of bone marrow aspirate are collected from human ilium, and after isolating Muse cells by using an antigen marker for SSEA-3 as an indicator, the cells are allowed to proliferate by culturing for an appropriate amount of time until an effective therapeutic dose is reached, followed by preparing autologous or allogenic Muse cells in the form of a cell preparation. Alternatively, for instance, Muse cells are isolated by using an antigen marker for SSEA-3 as an indicator, and then after the cells are allowed to proliferate by culturing for an appropriate amount of time until an effective therapeutic dose is reached, autologous or allogenic Muse cells can be prepared as a cell preparation.

In addition, when using the cell preparation of Muse cells, dimethylsulfoxide (DMSO) or serum albumin for protecting the cells, or antibiotics and the like for preventing contamination and growth of bacteria, may also be contained in the cell preparation. Moreover, other pharmaceutically allowable components (such as a carrier, vehicle, disintegrating agent, buffer, emulsifier, suspending agent, soothing agent, stabilizer, storage agent, preservative or physiological saline), or cells or components other than Muse cells contained in mesenchymal cells, may also be contained in the cell preparation. A person with ordinary skill in the art is able to add these factors and pharmaceutical agents to a cell preparation at suitable concentrations. In this manner, Muse cells can be used in the form of a pharmaceutical composition containing various types of additives.

The number of Muse cells contained in the cell preparation prepared in the manner described above can be suitably adjusted in consideration of the gender, age and body weight of the subject, disease state and state in which the cells are used so as to obtain the desired effect in treatment of cerebral infarction and sequelae (such as suppression of the progress of cerebral infarction, reduction of cerebral infarction volume, restoration of motility function, restoration of speech and language function, restoration of perceptual function). In Examples 3 and 4 to be subsequently described, a rat model of cerebral infarction was produced using an embolus, and various types of effects of transplanting Muse cells were examined. Extremely superior effects were obtained by administering SSEA3-positive cells to Wistar rats weighing about 200 to 300 g at $3\times10^4$ cells/animal. On the basis of this result, superior effects can be expected to be obtained by administering 1 to $1.5\times10^5$ cells/kg per individual mammal based on body weight. Here, examples of individuals include, but are not limited to, rats and humans. In addition, the cell preparation of the present invention may be administered a plurality of times (such as 2 to 10 times) at a suitable interval (such as twice per day, once per day, twice per week, once per week, once every two weeks, once every one month, one every two months, once every six months) until the desired therapeutic effect is obtained. Thus, although dependent upon the status of the subject, the therapeutically effective dose is preferably administered, for example, 1 to 10 times at $1\times10^3$ cells to $2\times10^7$ cells per individual. Although there are no particular limitations thereon, examples of total individual doses include $1\times10^3$ cells to $2\times10^8$ cells, $1\times10^4$ cells to $1\times10^8$ cells, $2\times10^4$ cells to $5\times10^7$ cells, $5\times10^4$ cells to $2\times10^7$ cells and $1\times10^5$ cells to $1\times10^7$ cells.

3. Preparation of Rat Cerebral Infarction Model

In the present description, a rat cerebral infraction model can be constructed and used to examine the therapeutic effects of the cell preparation of the present invention on cerebral infarction (including sequelae). Although there are no particular limitations of the rats of this model, typical examples thereof include Wistar rats and Spraque-Dawley rats. A cerebral infarction model can be created in order to promote symptoms resembling human cerebral infarction by inserting an embolus from the carotid artery of the rat, occluding the artery (such as the middle cerebral artery) leading to the brain tissue where cerebral infarction is to be induced for a prescribed amount of time with the embolus (to induce an ischemic state), and then extracting the embolus. Furthermore, the status of the cerebral infarction can be confirmed with a brain tissue section (following TTC staining). In addition, the cell preparation of the present invention has a heterologous relationship with the rats administered with the preparation since the Muse cells are of human origin. Normally, in experiments in which heterologous cells are administered to model animals, an immunosuppressant (such as cyclosporin) is administered either prior or simultaneous to administration of the heterologous cells in order to suppress an immune response in the body caused by the heterologous cells.

4. Therapeutic Effects of Muse Cells

In embodiments of the present invention, the cell preparation of the present invention is able to restore or return to normal brain function in patients suffering from cerebral infarction or patients suffering from sequelae thereof. When used in the present description, restoration of brain function refers to alleviation and inhibition of the progression of various functional disorders (including sequelae) accompanying cerebral infarction, and preferably refers to alleviation of functional disorders to a degree that they do not present a problem during the course of daily life. In addition, returning of brain function to normal refers to returning functional disorders (including sequelae) to the state prior to the onset of cerebral infarction. In addition, although there are no particular limitations thereon, evaluation of restoration of brain function is typically carried out by electrophysiological studies, neurological severity scores (NSS), imaging examinations and pathology studies. Here, "electrophysiological studies" refer to studies performed to carry out functional evaluations of various organs, including the brain, by observing a potential (waveform of an electrical signal) in response to an electrical stimulus with a prescribed apparatus in order to evaluate the function of the central nervous system, peripheral nervous system, muscle and the like. For example, in a study of the central nervous system (spinal cord), this potential is referred to as the somatosensory evoked potential (SEP), and the study consists of an examination for measuring the potential induced when a response induced by sensory stimulation of the limbs passes through a sensory pathway and is transmitted to the cerebral cortex. As a result, the degree of functional recovery of the central nervous system of a patient can be confirmed objectively following administration of the cell preparation of the present invention to the patient. In addition, the neurological severity score (NSS) is used to evaluate the degree of function of a damaged portion of the brain by scoring each parameter. An NSS for use in rats has been indicated by Chen, J. et al. (Stroke, Vol. 32, p. 1005-1111 (2001)).

Although the following provides a more detailed explanation of the present invention through examples thereof, the present invention is in no way limited by these examples.

EXAMPLES

Example 1: Preparation of Rat Cerebral Infarction Model

The "Regulations for Animal Experiments and Related Activities at Tohoku University" were strictly observed for the experimental protocol using rats in the present example, and experimental animals were prepared in accordance with these regulations under the supervision of the Tohoku University Experimental Animal Center. More specifically, a rat cerebral infarction model was prepared by inserting an embolus from the carotid artery of Wistar rats (males, age 10 weeks) and occluding a portion of the cerebral blood vessels (such as the middle carotid artery (MCA)). Subsequently, the embolus was extracted, the vessel was reperfused, and the rats were then used in the following experiments as a cerebral infarction model. Furthermore, the status of cerebral infarction was confirmed with brain tissue sections (following TTC staining). In addition, an immunosuppressant (FK506) was administered to the cerebral infarction rats prior to cell transplant since the transplanted Muse cells are heterologous with respect to rats.

Example 2: Preparation of Muse Cells

Preparation of human Muse cells derived from human fibroblasts was carried out in accordance with the method described in International Publication No. WO 2011/007900. More specifically, adhesive mesenchymal cells were cultured from human bone marrow fluid and after the cells proliferated, Muse cells or cell populations containing Muse cells were isolated by FACS as SSEA-3-positive cells. In addition, non-Muse cells consisted of a cell group negative for SSEA-3 present among the aforementioned mesenchymal cells, and were used as a control. Subsequently, the cells were adjusted to a prescribed concentration using phosphate-buffered physiological saline or culture liquid, and were used to evaluate the effects of Muse cells on brain function in the rat cerebral infarction model as indicated below. Furthermore, in the case of using cells obtained by culturing mesenchymal cells such as bone marrow-derived mesenchymal cells as a population of Muse cells, all SSEA-3-positive cells are known to be CD105-positive cells as reported by Wakao, et al. (2011, ibid).

Example 3: Evaluation of Brain Function by Transplanting Muse Cells

The cerebral infarction rats prepared in Example 1 were divided into three groups, and Muse cells ($1 \times 10^4$ cells, 2 µl PBS at 3 locations), non-Muse cells ($1 \times 10^4$ cells, 2 µl PBS at three locations) or physiological saline (6 µl) were injected directly into the cerebral parenchyma on day 2 following reperfusion. Subsequently, improvement of rat motor function was evaluated over time and cell kinetics were analyzed after a prescribed amount of time.

(1) Comprehensive Evaluation by Neurological Severity Score (NSS)

Various types of brain function disorders (such as paralysis, sensory disorders or vision disorders) were evaluated using the neurological severity score (NSS) (Chen, J., Stroke, Vol. 32, p. 1005-1111 (2001)) in the rats transplanted with cells as described above for a period of three months following transplant. In this evaluation using NSS, points were assigned for changes in motor function and as a result, a maximum score of 18 represents serious neurological dysfunction, while a score of 0 represents a normal neurological state. More specifically, evaluations were carried out on the following parameters consisting of: standing up with the tail (one point for each parameter (maximum of 3 points)), state when lying on the floor (0 to 3 points), sensory test (1 or 2 points), beam balance test (0 to 6 points) and reflex absence/motor impairment (maximum of 4 points). The results for the NSS scores of each group of rats (n=10) are shown in FIG. 1. In the non-Muse cell dose group and physiological saline dose group, scores decreased for about the first ten days after which scores tended to be maintained at 6 to 8 points. In contrast, in the Muse cell dose group, scores on day 20 were significantly lower in comparison with the other groups, and the scores tended to decrease further at the time the experiment was completed (80 days and beyond), with significant differences observed in comparison with the other groups.

(2) Rotarod Performance Test

Figure 2:
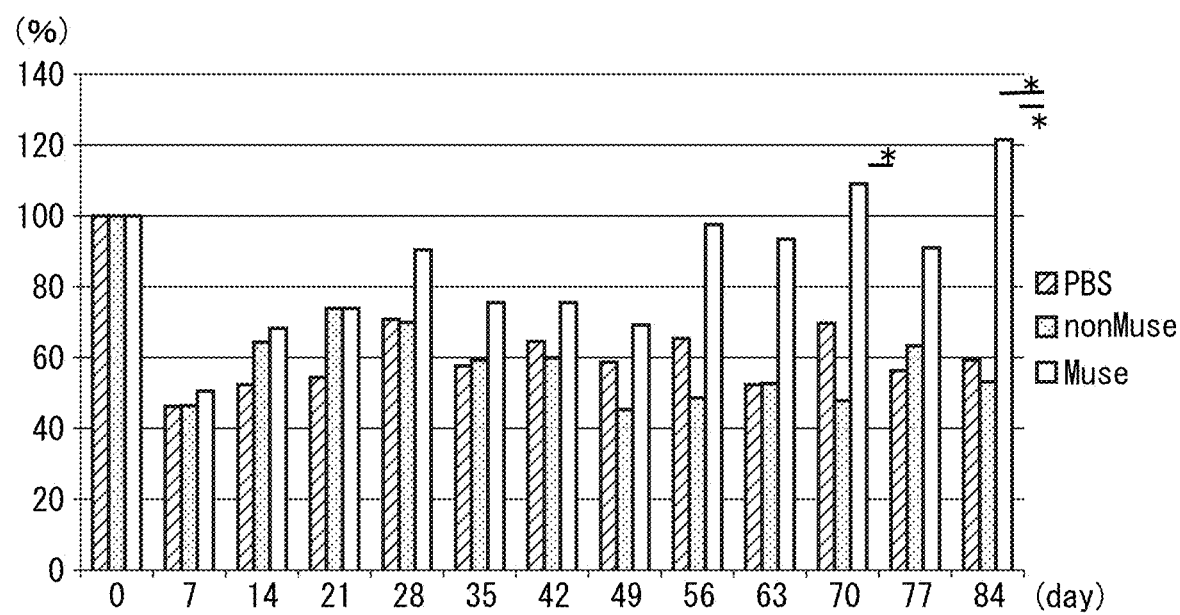
FIG. 2 indicates the results of a Rotarod performance test of motor function in a rat cerebral infarction model injected with Muse cells, non-Muse cells or phosphate-buffered saline (PBS). Recovery of motor function was observed over time based on the percentage of the average value of measured values (two) obtained on two measurement days by using two measured values obtained prior to transplant of Muse cells and the like as a baseline.

Restoration of cerebral dysfunction by transplantation of Muse cells was investigated using an apparatus commonly known to be used as an apparatus for measuring coordination of motor function and sense of balance in experimental animals. Evaluation in this test was carried out by measuring the amount of time until a rat fell off a rotating stand twice each day at a frequency of once a week (on days 0 to 84). The results are shown in FIG. 2. In the non-Muse cell dose group and physiological saline dose group, although roughly a maximum of 70% of motor function was observed to have been restored from days 21 to 28, motor function was not restored to 100% beyond that time. In contrast, in the Muse cell dose group, although scores temporarily decreased to 70% after initially recovering to 90% on day 28, motor function was observed to be restored to nearly 100% starting on day 56. On the basis of the comprehensive evaluation by NSS and the results of the Rotarod performance test as described above, Muse cells were suggested to remarkably improve brain function in cerebral infarction rats.

(3) Electrophysiological Studies

Figure 3:
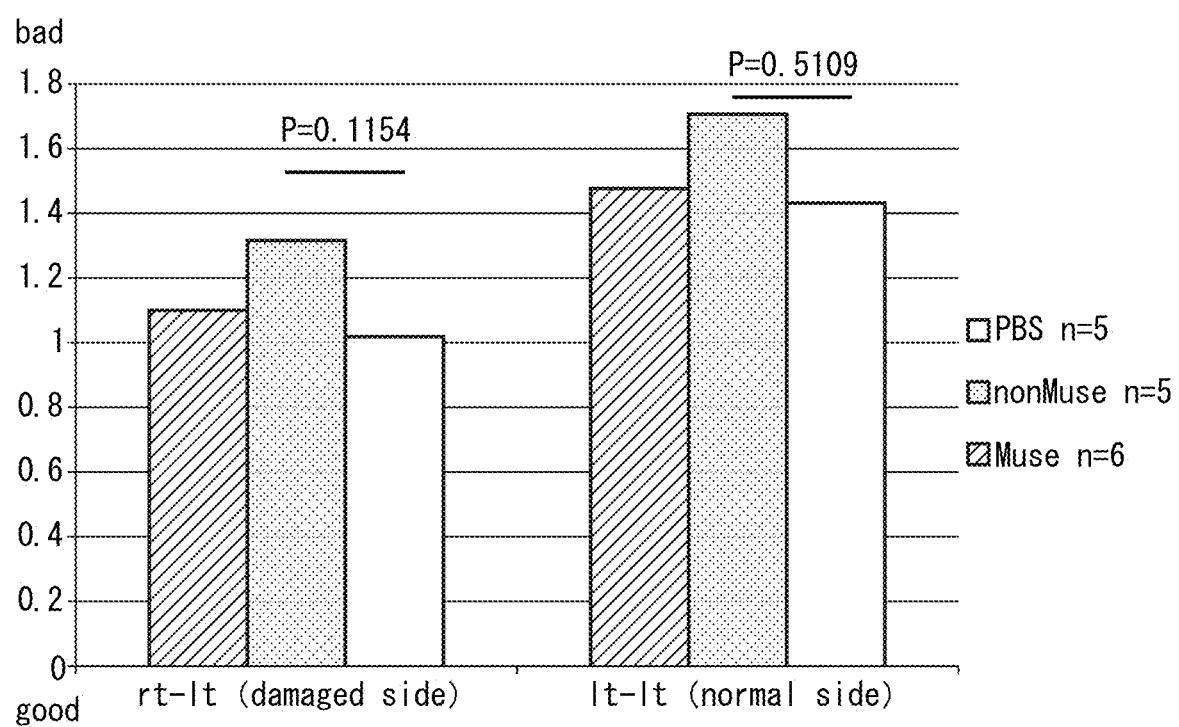

Somatosensory evoked potential (SEP) was measured in the rat cerebral infarction model 85 days after injection of Muse cells and the like (FIG. 3). The straight muscle of the thigh was stimulated at 10 mA and 1 Hz 100 times (at 1 second intervals), and potential was measured at a location 2.5 mm to the side and 2.5 mm posterior to the bregma at a depth of 1 mm. Right brain-left leg (rt-lt) indicates the latent time of stimuli traveling to the impaired side, while left brain-left leg (lt-lt) indicates the latent time of stimuli traveling to the same side of the brain, namely the healthy side. A shorter latent time indicates rapid recovery. In the group administered Muse cells, latent time was shorter than in the PBS or non-Muse cell group for both right brain-left leg (rt-lt) and left brain-left leg (lt-lt), and although statistically significant differences were not observed, the measured values suggested recovery of the neural network.

Example 4: Taking and Differentiation of Muse Cells in Brain Tissue

Figure 4:
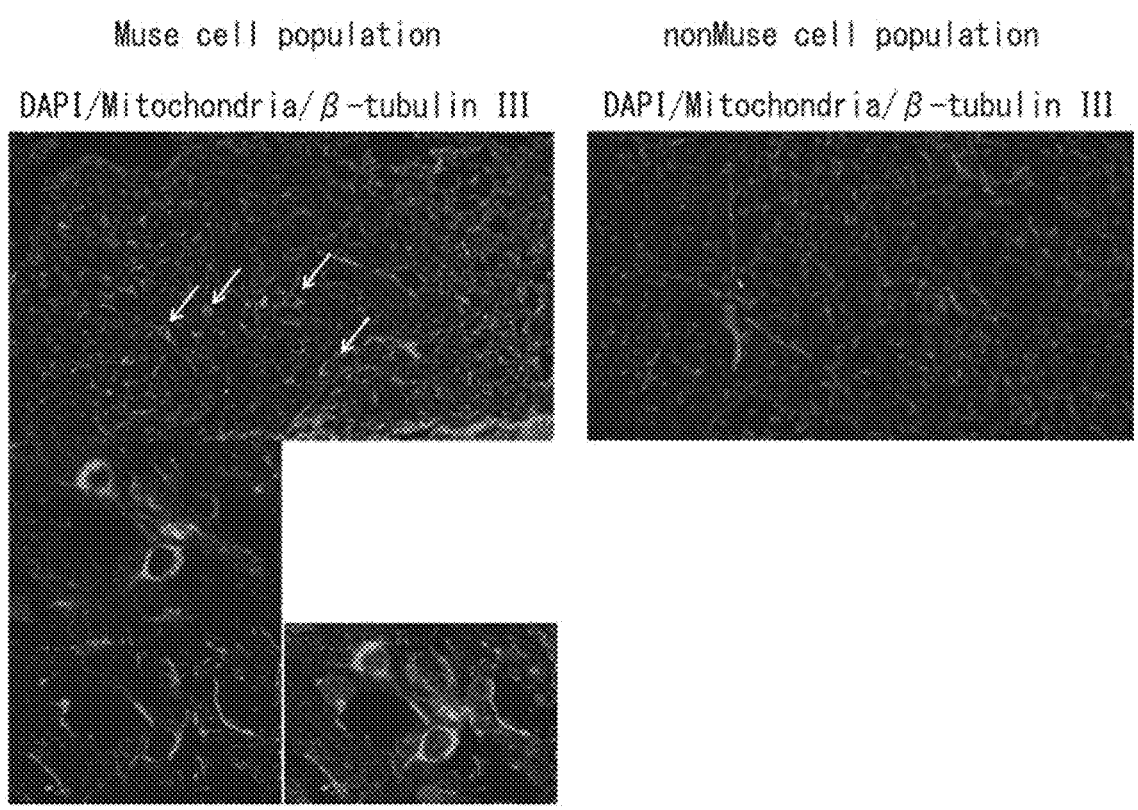
FIG. 4 indicates fluorescent images indicating taking and differentiation of Muse cells in brain tissue. Human-derived Muse cells were labeled green with human mitochondria marker, while nerve cells were labeled red using β-tubulin III as a marker. Muse cells injected into cerebral parenchyma were suggested to accumulate in a region bordering the infarction and differentiate into nerve cells after taking to that region. On the other hand, taking and differentiation of non-Muse cells were not observed.
Figure 5:
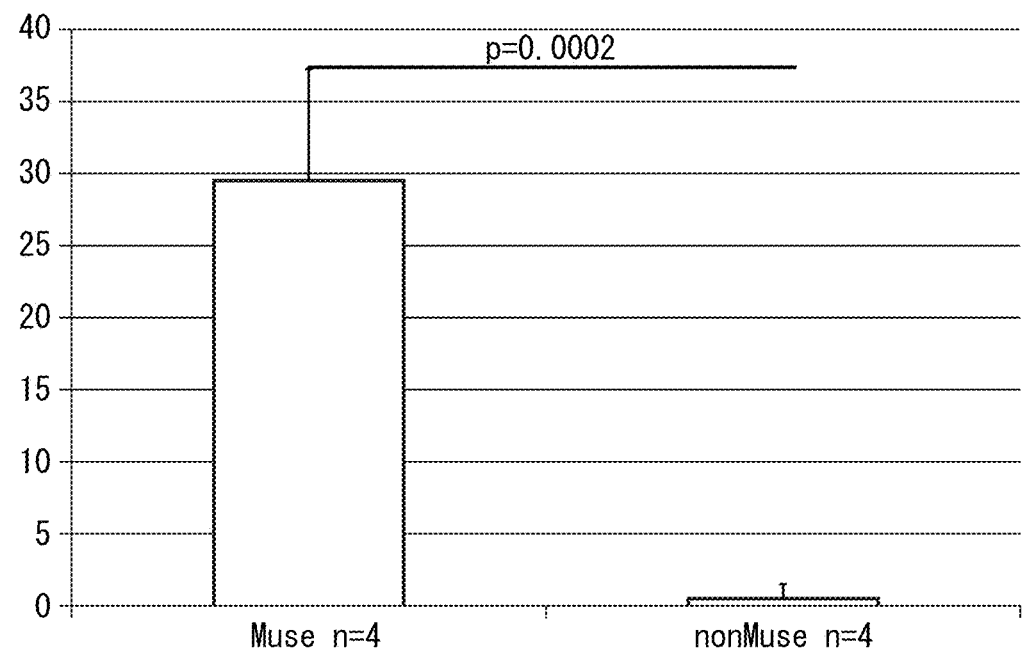
FIG. 5 indicates the results of observing human mitochondria marker-positive cells under a fluorescence microscope and respectively counting the number of cells contained in ten fields. Although hardly any non-Muse cells took to a region bordering the infarction, numerous Muse cells were present at that site.

A study was conducted as to whether or not Muse cells take to and differentiate into brain tissue in order to investigate the behavior of Muse cells and non-Muse cells injected into cerebral parenchyma. Brain tissue sections were prepared 85 days after administering these cells and then observed under a fluorescence microscope (FIG. 4). The cell nuclei of these sections were stained with DAPI followed by double-staining with human mitochondria marker and a nerve cell marker in the form of β-tubulin III. As a result, since fluorescence of the human mitochondria marker (green) and fluorescence of the β-tubulin III (red) indicating nerve cells were observed in the same cell group in brain sections of rats injected with Muse cells, Muse cells were suggested to take to brain tissue and differentiate into nerve cells. On the other hand, taking of non-Muse cells to brain tissue was not observed in brain tissue sections in the case of having injected non-Muse cells. In addition, in order to investigate the taking of Muse cells and non-Muse cells to a region bordering the infarction, human mitochondria marker-positive cells were observed under a fluorescence microscope and the numbers of each cell contained in 10 fields were respectively counted (FIG. 5). Although hardly any non-Muse cells took to the region bordering the infarction, numerous Muse cells were present. On the basis of these results, Muse cells were suggested to take to regions bordering on an infarction and differentiate into nerve cells in comparison with non-Muse cells.

INDUSTRIAL APPLICABILITY

The cell preparation of the present invention is able to regenerate brain cells (such as nerve cells or glial cells) at the site of a cerebral infarction by being administered into the cerebral parenchyma of a cerebral infarction model, is able to reduce infarct size and improve brain function, and can be applied to the treatment of cerebral infarction and to the prevention and/or treatment of sequelae following cerebral infarction.

All publications and patent documents cited in the present description are incorporated throughout the description by reference. Furthermore, although specific embodiments of the present invention have been explained in the present description for the purpose of exemplification, it can be easily understood by a person with ordinary skill in the art that the present invention may be modified in various ways without departing from the spirit and scope thereof.

What is claimed is:

1. A method for treating sequelae from a cerebral infarction in a mammalian subject in need thereof, the method comprising:
    administering a cell preparation containing human pluripotent stem cells positive for SSEA-3 isolated from human mesenchymal tissue or cultured human mesenchymal cells to the mammalian subject wherein said pluripotent stem cells have a plurality of properties, said plurality of properties comprising:
    (i) CD 105-positively;
    (ii) low or absent telomerase activity;
    (iii) ability to differentiate into any of the three germ layers;
    (iv) absence of demonstration of neoplastic proliferation;
    (v) self-renewal ability;
    wherein the sequelae is selected from the group consisting of speech and language disorder, disturbance of perception such as numbness, disorder of movement in a limb, headache, vomiting, visual loss, deglutition disorder, articulation disorder, and dementia; and
    wherein said pluripotent stem cells are administered 1 to 10 times at $1\times10^3$ cells to $2\times10^7$ cells per individual, or the total individual doses of said pluripotent stem cells are $1\times10^3$ cells to $2\times10^8$ cells or $1\times10^4$ cells to $1\times10^8$ cells, to treat sequelae from the cerebral infarction.

2. The method according to claim 1, wherein the pluripotent stem cells positive for SSEA-3 contain a concentrated cell fraction as a result of stimulation by external stress.

3. The method according to claim 1, wherein the pluripotent stem cells are CD117-negative and CD146-negative.

4. The method according to claim 1, wherein the pluripotent stem cells are CD117-negative, CD146-negative, NG2-negative, CD34-negative, vWF-negative and CD271-negative.

5. The method according to claim 1, wherein the pluripotent stem cells are CD34-negative, CD117-negative, CD146-negative, CD271-negative, NG2-negative, vWF-negative, Sox10-negative, Snail-negative, Slug-negative, Tyrpl-negative and Dct-negative.

6. The method according to claim 1, wherein the pluripotent stem cells have the ability to differentiate into one or more cells selected from the group consisting of nerve cells, glial cells, vascular endothelial cells, and/or microglial cells.

7. The method according to claim 1, wherein the cell preparation containing the pluripotent stem cells reduces infarct size by a mechanism involving regeneration of brain tissue.

8. The method according to claim 1, wherein the cell preparation containing the pluripotent stem cells improves or restores a brain dysfunction due to cerebral infarction by a mechanism involving regeneration of brain tissue.

9. A method for treating sequelae from a cerebral infarction in a mammalian subject in need thereof, the method comprising:
    administering to cerebral parenchyma of the mammalian subject a cell preparation containing human pluripotent stem cells positive for SSEA-3 isolated from human mesenchymal tissue or cultured human mesenchymal cells to the mammalian subject, wherein said pluripotent stem cells have a plurality of properties, said plurality of properties comprising:

(i) CD105-positively;
(ii) low or absent telomerase activity;
(iii) ability to differentiate into any of the three germ layers;
(iv) absence of demonstration of neoplastic proliferation;
(v) self-renewal ability, wherein the sequelae is selected from the group consisting of speech and language disorder, disturbance of perception such as numbness, disorder of movement in a limb, headache, vomiting, visual loss, deglutition disorder, articulation disorder, and dementia; and
wherein said pluripotent stem cells are administered 1 to 10 times at $1\times10^3$ cells to $2\times10^7$ cells per individual, or the total individual doses of said pluripotent stem cells are $1\times10^3$ cells to $2\times10^8$ cells or $1\times10^4$ cells to $1\times10^8$ cells, to treat sequelae from the cerebral infarction.

10. The method according to claim 9, wherein the pluripotent stem cells positive for SSEA-3 contain a concentrated cell fraction as a result of stimulation by external stress.

11. The method according to claim 9, wherein the pluripotent stem cells are CD117-negative and CD146-negative.

12. The method according to claim 9, wherein the pluripotent stem cells are CD117-negative, CD146-negative, NG2-negative, CD34-negative, vWF-negative and CD271-negative.

13. The method according to claim 9, wherein the pluripotent stem cells are CD34-negative, CD117-negative, CD146-negative, CD271-negative, NG2-negative, vWF-negative, Sox10-negative, Snail-negative, Slug-negative, Tyrpl-negative and Dct-negative.

14. The method according to claim 9, wherein the pluripotent stem cells have the ability to differentiate into one or more cells selected from the group consisting of nerve cells, glial cells, vascular endothelial cells, and/or microglial cells.

15. The method according to claim 9, wherein the cell preparation containing the pluripotent stem cells reduces infarct size by a mechanism involving regeneration of brain tissue.

16. The method according to claim 9, wherein the cell preparation containing the pluripotent stem cells improves or restores a brain dysfunction due to cerebral infarction by a mechanism involving regeneration of brain tissue.

17. The method according to claim 1, wherein the cell preparation containing the pluripotent stem cells is administered to cerebral parenchyma and accumulate in a region bordering the infarction and differentiate into nerve cells.

18. The method according to claim 9, wherein the cell preparation containing the pluripotent stem cells accumulate in a region bordering the infarction and differentiate into nerve cells.

19. The method according to claim 1, wherein the mammalian subject is a human.

20. The method according to claim 9, wherein the mammalian subject is a human.

21. The method according to claim 1, wherein the administration of the cell preparation improves motor function of the mammalian subject.

22. The method according to claim 9, wherein the administration of the cell preparation improves motor function of the mammalian subject.

23. The method according to claim 1, wherein the administration of the cell preparation is administered within 3 to 48 hours of infarction onset.

24. The method according to claim 9, wherein the administration of the cell preparation is administered within 3 to 48 hours of infarction onset.

* * * * *